United States Patent [19]

Anderson et al.

[11] Patent Number: 5,216,029
[45] Date of Patent: Jun. 1, 1993

[54] FISH PRODUCTION

[75] Inventors: David B. Anderson; Edward L. Veenhuizen, both of Greenfield, Ind.

[73] Assignee: Eli Lilly and Company, Indianapolis, Ind.

[21] Appl. No.: 798,679

[22] Filed: Nov. 26, 1991

[51] Int. Cl.$^5$ ............................ A61K 31/135
[52] U.S. Cl. ................................... 514/653
[58] Field of Search ........................... 514/653

[56] References Cited

U.S. PATENT DOCUMENTS

| | | | |
|---|---|---|---|
| 4,690,951 | 9/1987 | Anderson et al. | 514/653 |
| 4,734,437 | 3/1988 | Anderson et al. | 514/653 |
| 4,849,453 | 7/1989 | Anderson et al. | 514/653 |
| 4,904,662 | 2/1990 | Anderson et al. | 514/237.8 |
| 4,992,473 | 2/1991 | Anderson et al. | 514/653 |

FOREIGN PATENT DOCUMENTS

| | | |
|---|---|---|
| 103830 | 3/1984 | European Pat. Off. . |
| 3234995 | 9/1982 | Fed. Rep. of Germany . |
| 2647310 | 11/1990 | France . |

OTHER PUBLICATIONS

Derwent 84-076585/13.
Derwent 84-083570/14.

*Primary Examiner*—Frederick E. Waddell
*Assistant Examiner*—K. Weddington
*Attorney, Agent, or Firm*—Kathleen R. S. Page; Leroy Whitaker

[57] ABSTRACT

This invention is directed to the use of the compound ractopamine for improved production of fish.

16 Claims, No Drawings

FISH PRODUCTION

BACKGROUND OF THE INVENTION

Extensive fishing of natural waters has lead to a reduction in fish numbers. It is now recognized that fishing at a rate to sustain natural populations will not provide the world's needs for fish as a food. This has lead to the development of the aquaculture industry, in which fish and other aquatic species are produced in controlled bodies of water. Fish is, worldwide, the single biggest source of protein, and aquaculture is therefore an increasingly important means of producing food. Furthermore, since the fish are in a controlled body of water, means are being sought to control disease and maximize production. The present invention provides a new technique for improved fish production.

BRIEF SUMMARY OF THE INVENTION

The present invention is directed to a method for improved fish production, comprising the step of administering an effective amount of the compound ractopamine or a physiologically acceptable salt thereof.

Ractopamine is the USAN name for the compound 4-hydroxy-α-(((3-(4-hydroxyphenyl)-1-methylpropyl)amino)methyl)benzenemethanol, having the following structural formula:

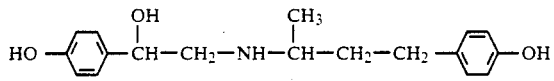

Ractopamine is prepared by art procedures, see U.S. Pat. No. 4,690,951, which is incorporated herein by reference. In the present invention, it can be used as such or as a physiologically acceptable salt thereof, preferably the hydrochloride. The compound has two asymmetric carbon atoms. The R,R isomer is the most active but other isomers are also active and resolution is not necessary. Most preferably, a mixture of optical isomers is used.

The use of ractopamine in fish production leads to numerous improvements, though not all such improvements will be obtained in every embodiment of the invention. In many instances, the practice of the present invention results in an improved growth rate and/or higher feed efficiency. The invention can also be used to reduce the percentage of fat in fish. The practice of the invention can also lead to improved flavor or texture, and other benefits.

By "fish" is meant any member of the Phylum Chordata, Sub Phylum Vertebrata, and Super Class Pisces. The present invention can be practiced with any of the considerable variety of fish species. Representative species include the following:

Catfish
    Channel Catfish (*Ictalurus punctatus*)
    Black Bullhead (*Ictalurus melas*)
    Yellow Bullhead (*Ictalurus natalis*)
    Brown Bullhead (*Ictalurus nebulosus*)
Carp (*Cyprinus carpio*)
Crucian Carp (*Carassius carassius*)
Trout
    Rainbow (formerly called *Salmo gairdneri*, now called *Oncorhynchus mykiss*)
    Brown (*Salmo trutta*)
    Speckled brook (*Salvelinus fontinalis*)
Salmon
    Atlantic (*Salmo salar*)
    Coho (*Oncorhynchus kisutch*)
    Chinook or King Salmon (*Onorhynchus tshawytscha*)
Tench (*Tinca tinca*)
Roach (*Rutilus rutilus*)
Pike (*Esox lucius*)
Pike-Perch (*Lucioperca Iucioperca*)
Dover Sole
Turbot
Yellowtail (*Seriola quinqueradiata*)
Bass
    Smallmouth (*Micropterus dolomieui*)
    Largemouth (*Micropterus salmoides*)
    Striped (*Morone saxatilis*)
Milkfish (*Chanos chanos*)
Tilapia (Sarotherodon sp.)
Tilapia (Tilapia sp.)
Gray Mullet (*Mugil cephalus*)
Eels
    American (*Anguilla rostrata*)
    European (*Anguilla anguilla*)
    Japanese (*Anguilla japonicus*)

Yet other species with which the present invention can be practiced will be apparent to those skilled in the art.

In aquaculture, a practical mode of delivering a substance is in the feed. Indeed, fish feeds are a standard article of commerce, often tailored for an individual species. Typically, the feed is in the form of small pellets. Therefore, in practicing the present invention, while other routes of delivery can be employed, the preferred method of delivery is in a nutritionally balanced complete fish food. The ractopamine or physiologically acceptable salt is dispersed in the fish food by known techniques.

The amount of ractopamine or salt to be employed will vary with the specific improvement desired, the fish species, the age of the fish, and other factors known to those in the field of aquaculture. In general, a concentration in the fish food of from 1 to 100 ppm will provide good results. In many instances, concentrations in the range of 5-20 ppm will suffice.

The invention is illustrated by the following examples.

Experiment 1

Ractopamine hydrochloride in Catfish

Full-sibling, year-2 channel catfish fingerlings averaging 91 g were stocked into nine 1-m³ circular raceways with continuously-flowing (6 L/min) water supplied from an earthen reservoir. The fish were stocked at the rate of 50 fish per raceway and all fish were fed a high perfomance feed (36% crude protein, 3.2 kcal digestible energy/g) (Table 1) for 5 weeks until the fish reached an average weight of 156 g. At this time, the raceways were randomly assigned to three experimental groups; one group continued to receive the control feed and the other groups were fed the control feed supplemented with 20 or 100 ppm of ractopamine. The feeds were prepared by regrinding the ingredients through a 2-mm diameter screen, mixing, and processing into 6 mm-diameter pellets with a laboratory pellet mill. The fish were fed the experimental diets to satiation two times daily, at 0900 and 1800 hours, for 4 weeks, then weighed and fed for an additional 2 weeks. At the end of the feeding period, 10 fish were randomly sampled from each raceway for measurement of dressing yield, mesenteric fat, and muscle composition. Minimum and maximum daily water temperatures during the first 4 weeks of the experiment averaged 29° and 31° C. and during the last 2 weeks averaged 24° and 26° C.

Analytical Procedures

Skin, head and viscera were removed from each of the sampled fish and dressing yield (dressed weight as a percentage of whole fish weight) was determined. Mesenteric fat was separated from other viscera and weighed. Muscle from one side of each fish was removed for analysis of crude protein (Kjeldahl procedure), crude fat [Gerber procedure as described in Association of Official Analytical Chemists. (1984). Official methods of analysis. 14th edition. Arlington, Va.] and moisture. Differences among treatments in weight gain (4 weeks and 6 weeks), dressing yield, mesenteric fat, and muscle composition were tested by one-way analysis of variance and selected treatment comparisons (ractopamine versus control, high ractopamine versus low ractopamine) were made [Steel, R. G. & Torrie, J. H. (1980). Principles and procedures of statistics. A biomedical approach. 2nd edition. McGraw-Hill Book Company, New York]. Differences are considered significant at $P<0.05$. Results are set forth in Tables 2 and 3.

TABLE 1
INGREDIENT AND NUTRIENT COMPOSITION OF THE BASAL DIET

| Item | Amount |
|---|---|
| Ingredient (g/100 g): | |
| Menhaden fish meal | 12.0 |
| Dehulled soybean meal | 53.5 |
| Wheat midlings | 10.0 |
| Corn | 21.2 |
| Dicalcium phosphate | 1.0 |
| Trace mineral premix[1] | 0.1 |
| Vitamin premix[2] | 0.2 |
| Menhaden oil | 2.5 |
| Nutrient: | |
| Crude protein (%) | 36.2 |
| Crude fat (%) | 5.7 |
| Digestible energy (kcal/g) | 3.2 |
| P/E (mg protein/kcal DE) | 11 |

[1]Trace mineral mix was the same as described by Reis et al. [(1989). Protein-to-energy ratios in production diets and growth and body composition to channel catfish. Aquaculture. 77:21-27] and provided the following (mg/kg of diet): Zn. 150; Fe, 44; Mn. 25; I, 5; Cu, 3; Se, 0.25.
[2]Vitamin premix provided the following (mg/kg diet): thiamin, 20; choline chloride, 2,000; niacin, 150; riboflavin, 20; pyridoxine, 20; folic acid, 5; calcium pantothenate, 200; cyanocobalamin, 0.06; retinol as (retinyl acetate) 4,000; all-rac-alpha-tocopherol, 50; cholecalciferol (1,000,000 IU/g), 2; menadione, 10; biotin, 1; L-ascorbic acid, 100; ethoxyquin (an antioxidant), 200.

TABLE 2
AVERAGE WEIGHT INCREASE BY YEAR-2 CHANNEL CATFISH FED RACTOPAMINE FOR 4 WEEKS AND FOR AN ADDITIONAL 2 WEEKS

| Dietary Ractopamine (ppm) | Fish Weight (g) | | | Percentage Weight Increase | |
|---|---|---|---|---|---|
| | Initial | 4 Week | 6 Week | Wk 0–4 | Wk 4–6 |
| 0 | 146 | 265 | 325 | 81.5 | 22.6 |
| 20 | 163 | 318 | 373 | 95.0 | 17.3 |
| 100 | 168 | 319 | 377 | 89.8 | 18.1 |

| F test: Contrast | 0–4 Weeks | 4–6 Weeks |
|---|---|---|
| Control vs ractopamine | p<0.05 | NS |
| Low ractopamine vs high ractopamine | NS | NS |

NS = not statistically significant

TABLE 3
MESENTERIC FAT, MUSCLE COMPOSITION AND DRESSING PERCENTAGE FOR YEAR-2 CHANNEL CATFISH FED RACTOPAMINE FOR 6 WEEKS IN RACEWAYS

| Dietary ractopamine (ppm) | Mesenteric fat (g/100 g body wt.) | Muscle | | | Dressing Percentage |
|---|---|---|---|---|---|
| | | Fat (%) | Protein (%) | Moisture (%) | |
| 0 | 3.2 ± 0.4a | 8.4 ± 1.4 | 16.8 ± 2.2 | 73.7 ± 6.1 | 66.8 ± 0.5 |
| 20 | 2.6 ± 0.2b | 6.3 ± 1.3 | 16.6 ± 0.6 | 76.0 ± 6.9 | 65.5 ± 0.1 |
| 100 | 2.6 ± 0.1b | 5.6 ± 0.3 | 16.4 ± 0.6 | 76.8 ± 7.1 | 66.0 ± 0.3 |

| F. test: Contrast | Mesenteric fat | Muscle fat | Muscle protein | Muscle moisture | Dressing percentage |
|---|---|---|---|---|---|
| Control vs ractopamine | P<0.05 | P<0.05 | NS | P<0.05 | P<0.05 |
| Low ractopamine vs high ractopamine | NS | NS | NS | NS | P<0.05 | a,b: different letters indicate a statistically significant difference.
NS = not statistically significant

Discussion

During the initial 4-week period, the fish fed ractopamine gained significantly more weight than the control (Table 2). There was no difference in weight gain between 20 and 100 ppm of ractopamine. During the following 2-week period there was no difference in weight gain among treatments. Water temperature in the outdoor raceways had begun to decrease at the beginning of the second feeding period and could have been a factor.

Feeding ractopamine significantly reduced the amount of mesenteric fat in the fish; however, there was no effect of increasing ractopamine from 20 to 100 ppm (Table 3). Feeding ractopamine also significantly reduced percentage of fat in the muscle of the fish (Table 3). Increasing ractopamine from 20 to 100 ppm effected a slight further decrease in percentage muscle fat (which, however, was not statistically significant). Moisture content of the muscle increased as fat decreased. Protein percentage of the wet muscle was not different among treatments; however, on a moisture-free basis there was a significantly higher percentage of protein in muscle of the ractopamine fed fish. Dressing percentage was significantly higher in the control fish.

and stored at 5° C. until fed. Fish were fed to near satiation, twice daily for 12 weeks. Feed consumption and water quality (dissolved oxygen, total gas pressure, pH and ammonia) were recorded weekly. Fish were weighed and feed conversion was calculated every four weeks. Daily behavioral and health/morbidity/mortality records were also kept. Results were as set forth in the following tables.

TABLE 4

EFFECTS OF RACTOPAMINE (LEAST SQUARE MEANS ± SEM) ON ABSOLUTE WEIGHT GAIN/FISH (G) DURING THREE TREATMENT PERIODS

| Level in Diet (ppm) | Weeks 1–4 | Weeks 4–8 | Weeks 8–12 | Ave. Over Weeks |
|---|---|---|---|---|
| 0  | 86.80 ± 2.32  | 74.51 ± 2.67   | 92.13 ± 5.24 | 85.02 ± 2.21 |
| 5  | 87.86 ± 2.29  | 82.00 ± 2.65[b]| 89.70 ± 5.99 | 87.45 ± 2.27 |
| 10 | 93.83 ± 2.51[a]| 80.57 ± 2.21  | 92.66 ± 5.30 | 89.82 ± 2.26 |
| 20 | 83.44 ± 2.58  | 74.10 ± 2.21   | 96.93 ± 5.55 | 85.49 ± 2.39 |
| 40 | 87.55 ± 2.28  | 79.71 ± 2.21   | 99.22 ± 5.20 | 89.32 ± 2.27 |

[a] Within the same column, different from controls ($p \leq 0.05$)
[b] Within the same column, different from controls ($p \leq 0.1$)

TABLE 5

EFFECTS OF RACTOPAMINE (LEAST SQUARE MEANS ± SEM) ON FEED INTAKE/FISH (G) OVER THREE TREATEMENT PERIODS

| Level in Diet (ppm) | Weeks 1–4 | Weeks 4–8 | Weeks 8–12 | Ave. Over Weeks |
|---|---|---|---|---|
| 0  | 107.89 ± 1.78    | 111.75 ± 2.55 | 144.40 ± 3.39 | 121.09 ± 1.50 |
| 5  | 108.76 ± 1.75    | 107.13 ± 2.48 | 145.77 ± 3.79 | 120.77 ± 1.51[a] |
| 10 | 101.86 ± 1.74[b] | 107.16 ± 2.41 | 138.75 ± 3.38 | 115.89 ± 1.46 |
| 20 | 112.81 ± 1.73[c] | 113.83 ± 2.75 | 146.02 ± 3.45 | 124.78 ± 1.51[c] |
| 40 | 107.65 ± 1.74    | 108.80 ± 2.83 | 137.74 ± 3.31 | 118.80 ± 1.51 |

[a] Within the same column, different from controls ($p \leq 0.01$)
[b] Within the same column, different from controls ($p \leq 0.05$)
[c] Within the same column, different from controls ($p \leq 0.1$)

TABLE 6

EFFECTS ON RACTOPAMINE (LEAST SQUARE MEANS ± SEM) ON FEED CONVERSION (G FEED/G GAIN) OVER THREE TREATMENT PERIODS

| Level in Diet (ppm) | Weeks 1–4 | Weeks 4–8 | Weeks 8–12 | Ave. Over Weeks |
|---|---|---|---|---|
| 0  | 1.25 ± 0.03    | 1.49 ± 0.06    | 1.58 ± 0.09 | 1.44 ± 0.04 |
| 5  | 1.23 ± 0.03    | 1.33 ± 0.06[b] | 1.61 ± 0.1  | 1.38 ± 0.04 |
| 10 | 1.15 ± 0.03[a] | 1.39 ± 0.06    | 1.56 ± 0.09 | 1.37 ± 0.04 |
| 20 | 1.28 ± 0.03    | 1.47 ± 0.07    | 1.46 ± 0.09 | 1.40 ± 0.04 |
| 40 | 1.23 ± 0.03    | 1.37 ± 0.07    | 1.45 ± 0.09 | 1.35 ± 0.04[b] |

[a] Within the same column, different from controls ($p \leq 0.05$)
[b] Within the same column, different from controls ($p \leq 0.1$)

Feed efficiency was not calculated because accurate measurement of food consumed could not be made since the pellets sank to the bottom of the raceways when fed.

Experiment 2

Ractopamine in Rainbow Trout at 5–40 ppm in Diet

Rainbow trout were sorted into groups weighing 150–200 g. Thirty-two fish were randomly assigned to each of 20 experimental tanks (capacity 60 L water). Fish weights per tank were then balanced prior to initiation of the trial in order to minimize between tank variation. The tanks were aerated and maintained on a single pass, flow-through system with flow rate set at 2.5 L/min. Water temperature was continuously electronically monitored. Five diets with levels of ractopamine at 0, 5, 10, 20 and 40 ppm were formulated using a previously pelleted, commercial diet, steam pelleted to 4.0 mm, and dried for 24 hours. The diets were sieved

We claim:

1. A method of improving the production of fish in which the improvement is enhanced growth, higher feed efficiency, reduced fat deposition, or improved flavor or texture, which comprises administering to the fish an effective amount of an active agent which is ractopamine or a physiologically acceptable salt thereof.

2. The method of claim 1 wherein the fish is a catfish.

3. The method of claim 1 wherein the fish is a carp.

4. The method of claim 1 wherein the fish is a salmon.

5. The method of claim 1 wherein the fish is a trout.

6. The method of claim 1 wherein the fish is a yellowtail.

7. The method of claim 1 wherein the fish is a striped bass.

8. The method of improving the production of fish which comprises administering to the fish a nutritionally balanced fish food comprising 1-100 ppm of an active agent which is ractopamine or a physiologically acceptable salt thereof.

9. The method of claim 8 employing a fish food comprising 5-20 ppm of the active agent.

10. The method of claim 9 wherein the active agent is ractopamine hydrochloride.

11. The method of claim 10 wherein the fish is a catfish.

12. The method of claim 10 wherein the fish is a carp.

13. The method of claim 10 wherein the fish is a salmon.

14. The method of claim 10 wherein the fish is a trout.

15. The method of claim 10 wherein the fish is a yellowtail.

16. The method of claim 10 wherein the fish is a striped bass.

* * * * *